United States Patent [19]

Chamuel

[11] Patent Number: 4,586,381

[45] Date of Patent: May 6, 1986

[54] NONDESTRUCTIVE ULTRASONIC TRANSDUCER

[75] Inventor: Jacques R. Chamuel, Framingham, Mass.

[73] Assignee: The Charles Stark Draper Laboratory, Inc., Cambridge, Mass.

[21] Appl. No.: 518,528

[22] Filed: Jul. 29, 1983

[51] Int. Cl.⁴ .......................................... G01N 29/04
[52] U.S. Cl. ........................................ 73/643; 73/644
[58] Field of Search ................. 73/600, 618, 643, 644, 73/661, DIG. 2; 310/26, 336; 376/249, 252

[56] References Cited

U.S. PATENT DOCUMENTS

| | | | |
|---|---|---|---|
| 2,912,854 | 11/1959 | Schubring | 73/644 |
| 3,089,333 | 5/1963 | Kleesattel | 73/661 |
| 3,302,044 | 1/1967 | Lynnworth et al. | 310/336 |
| 3,580,057 | 5/1971 | Seegmiller | 310/336 |
| 3,924,456 | 12/1975 | Vahaviolos | 73/770 |
| 4,035,762 | 7/1977 | Chamuel | 73/609 |
| 4,137,779 | 2/1979 | Wustenberg et al. | 73/627 |
| 4,308,751 | 1/1982 | Thurner et al. | 73/627 |
| 4,313,070 | 1/1982 | Fisher | 73/644 |
| 4,352,038 | 9/1982 | Moreton | 73/587 |
| 4,442,714 | 4/1984 | Bongianni | 73/643 |
| 4,461,178 | 7/1984 | Chamuel | 73/599 |

OTHER PUBLICATIONS

Kaule, W., "Dry Ultrasonic Testing", in Issue 13 of the Echo, Krautkramer News on Nondestructive Testing with Ultrasonics, Jan., 1965.

Primary Examiner—Stewart J. Levy
Assistant Examiner—John E. Chapman, Jr.

Attorney, Agent, or Firm—Weingarten, Schurgin Gagnebin & Hayes

[57] ABSTRACT

An extendable probe that permits nondestructive ultrasonic inspection of a workpiece for flaws is disclosed which provides information indicative of flaw presence and location. The probe includes a pair of waveguides capable of elastic wave transmission. A first waveguide is excited to produce elastic waves which travel along the waveguide to an end of the waveguide in elastic wave transmitting contact with the surface of the workpiece under inspection. A second waveguide is maintained in contact with the workpiece a selected distance from the first waveguide and a sensor is disposed on the second waveguide for reception of elastic waves. In the absence of workpiece defects intermediate the contact points of the first and second waveguides, elastic waves are transmitted from the first waveguide to the second waveguide through the workpiece to the sensor and an output signal representative of transmitted elastic waves is produced by the sensor. The presence of a crack or flaw in the workpiece between or proximate to respective ends of the waveguides is apparent as a variation in the amplitude of the sensor output signal.

Inspection of relatively inaccessible remote surfaces is facilitated with the probe which is thin and extendable. The distance from the sensors to a workpiece flaw is determinable from travel time of elastic waves in the waveguides and the workpiece.

Detection of flaws of varied orientation in the workpiece is achieved by pivotable orientation of the waveguide ends with respect to the workpiece.

21 Claims, 5 Drawing Figures

NONDESTRUCTIVE ULTRASONIC TRANSDUCER

FIELD OF THE INVENTION

This invention relates to apparatus and methods for nondestructive detection and location of flaws or defects in surfaces of a workpiece.

BACKGROUND OF THE INVENTION

Defects existing in walls or surfaces of mechanical systems and structures can result in system failures and in certain circumstances can produce catastrophic effects. Consequently, in situations where mechanical integrity is of prime importance it is desirable to be able to nondestructively inspect surfaces or walls of important structures and to perform preventative maintenance or reduce operational loads or otherwise reduce the potential hazards of failure before such failures occur.

Inspection of specific walls and surfaces may be difficult as a consequence of surface inaccessibility or resulting from the location of the surface within a hazardous environment such as within the containment area of a nuclear reactor. In these situations it is necessary to provide for nondestructive inspection from a remote location and to provide information indicative of both the presence and location of defects.

An acoustic waveguide assembly used for predicting the failure of structured members under stress is disclosed in U.S. Pat. No. 4,352,038.

U.S. Pat. No. 4,308,751 discloses a method for nondestructive testing of rock anchors embedded in stone. The exposed end of the anchor is excited with a source of elastic waves and reflected waves analyzed to assess the integrity of the anchor and its load bearing capabilities.

Another nondestructive inspection process is disclosed in U.S. Pat. No. 3,924,456 in which a workpiece is subjected to stress, and stress waves are observed employing a stress wave sensor to determine the presence of any cracks or defects.

None of the methods previously disclosed are adapted for inspection of a wall or workpiece surface, where the surface to be inspected may be physically inaccessible, or located in a remote location. Furthermore, none of the art disclosed provides simultaneous information indicative of both the presence and location of a defect in a workpiece surface.

SUMMARY OF THE INVENTION

In accordance with the teaching of the present invention, an extendable probe is disclosed which permits remote inspection of a workpiece for cracks, flaws, or other defects and provides information indicative of defect location. The probe in one embodiment includes first and second magnetostrictive waveguides, one end of each waveguide being in physical contact with the workpiece. The distance between points of contact of the respective waveguide ends with the workpiece is typically fixed by a support separating respective ends of the waveguide. A source of elastic waves is slideably disposed about the first magnetostrictive waveguide. (See U.S. Pat. No. 4,035,762 of same inventor and assignee). Upon actuation, the source induces elastic waves within the first waveguide and the elastic waves are transmitted through the first waveguide to a point of contact of the first waveguide with the workpiece. In a non-flawed workpiece, elastic waves are transmitted through the workpiece to a point of contact of the second waveguide with the workpiece, a selected distance from the first waveguide point of contact. The elastic waves travel through the second magnetostrictive waveguide and are received by a sensor slideably disposed about the waveguide. In a non-flawed workpiece, an elastic wave induced in the first waveguide is received at the sensor at a fixed time after inducement within the first waveguide, the period being determined by the time of propagation through the respective waveguides and the workpiece. The presence of a crack or flaw between respective waveguide contact points varies the transmission characteristics of elastic waves from the first waveguide to the second waveguide thereby altering the amplitude and time of the received signal at the sensor.

The delay time between elastic wave inducement in the first waveguide and elastic wave detection by the sensor is determined by the propagation velocity of the elastic waves through the respective waveguides and the workpiece, is nearly proportional to waveguide length, and is thus indicative of the distance to an observed flaw or defect.

The points of contacts may be moved and the orientation varied to inspect all areas of a surface accessible by slideable movement of the waveguide ends.

The waveguides are typically slideably disposed in a sheath having an acoustic mismatch with the first and second waveguides such that elastic waves present in the waveguide are not dampened or shunted due to contact of the respective waveguide with the sheath. Since the source of induced elastic waves, the elastic wave sensor, and the sheath are slideably disposed with respect to the magnetostrictive waveguides, the distance from the elastic wave source and sensor to the workpiece may be varied by sliding the respective waveguides through the respective source, sensor, and sheath to vary the distance to the point of inspection. Additionally, inspection for horizontal or vertical cracks may be achieved by pivotable orientation of the respective waveguide contact points by differential movement of the respective waveguides within the sheath.

The disclosed invention is particularly applicable for inspection of surfaces in confined areas, for inspection of surfaces which are not readily accessible to visual inspection, or for remote inspection of surfaces.

DESCRIPTION OF THE DRAWINGS

The invention will be more fully understood from the following description taken in conjunction with the accompanying drawings, in which.

DETAILED DESCRIPTION OF THE INVENTION

Figure 1:
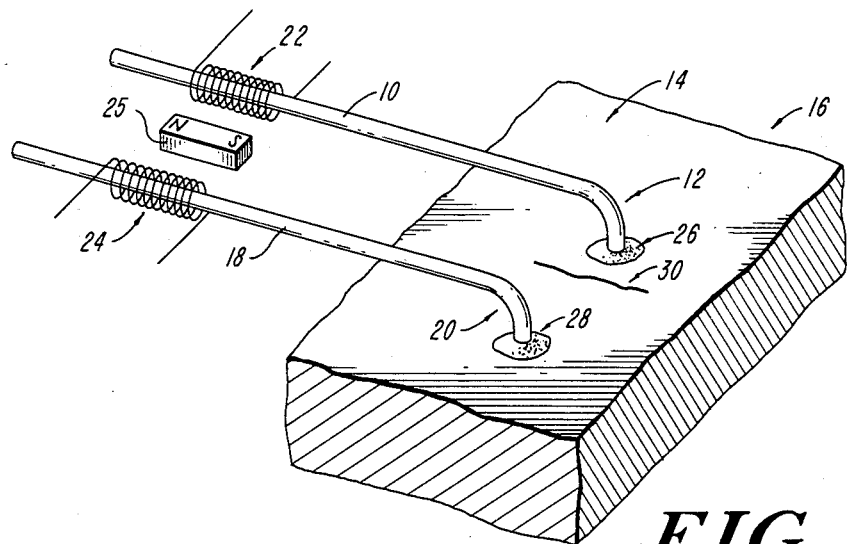
FIG. 1 is a schematic view of the non-destructive inspection probe in accordance with the present invention.

A method and apparatus is disclosed for detection of flaws in a workpiece by non-destructive ultrasonic inspection means. The invention will be clearly understood by reference to FIGS. 1-3B.

A preferred embodiment of the present invention comprises a probe including a first magnetostrictive waveguide 10 having an end 12 in elastic wave transmitting contact with a surface 14 of a workpiece 16. The probe also includes a second magnetostrictive waveguide 18 having an end 20 contacting the workpiece surface 14 a selected distance from the point of contact of end 12 of the first waveguide 10 with the workpiece 16. The waveguides 10 and 18 may be any magnetostrictive material, such as a nickel wire. A first coil 22 is disposed about the first waveguide 10 and serves to generate elastic waves in the first waveguide 10. A second coil 24 is disposed about the second waveguide 18 and acts as a sensor operative to convert elastic waves present in the second magnetostrictive waveguide 18 to an output signal representative of the elastic waves. Magnetic bias for improved magnetic induction may be provided by a magnet 25 or any other suitable magnetic field source. (See U.S. Pat. No. 4,035,762 of same inventor and assignee).

In operation, an electrical pulse is applied to the first coil 22. The coil may vary in the number of turns, however, in the present example the coil is illustrated as having thirty turns around the first magnetostrictive waveguide. The electrical pulse applied to the coil 22 may vary greatly in current and duration, but for purposes of illustration is presently taught to be 0.4 amps and of 20 microsecond duration. An induced magnetic field is produced as a consequence of the pulse actuation of the coil 22 and produces an elastic wave in the first magnetostrictive waveguide 10 due to the interaction of the induced magnetic field with the magnetostrictive waveguide 10. The elastic wave produced by pulse actuation of the coil 22 travels through the magnetostrictive waveguide 10 to the end 12 in physical contact with the workpiece 16. Typically, to improve coupling of the magnetostrictively generated elastic wave with the workpiece 16, conventional ultrasonic coupling materials are employed to form an ultrasonic coupling contact 26 between the magnetostrictive waveguide 10 and the workpiece surface 14. The ultrasonic coupling contact 26 is provided by the use of an elastomer, jelly, grease, or any other suitable fluid. In the absence of a flaw or crack, the elastic wave is transmitted through the first magnetostrictive waveguide 10, to the workpiece surface 14 and through the workpiece surface 14 to the point of physical contact of end 20 of the second magnetostrictive waveguide 18 with the workpiece surface 14. A similar ultrasonic coupling contact 28 is provided between the workpiece surface 14 and end 20 of the magnetostrictive waveguide 18 to improve transmission of elastic waves from the surface 14 to the waveguide 18. Elastic waves travel through the surface 14 in the absence of a defect between respective contacts 26 and 28 and travel through the second magnetostrictive waveguide 18 to the transducer 24 which converts elastic waves present in the waveguide to an electrical output signal representative of the received waves.

The presence of a defect 30 between or proximate to respective contact points 26 and 28 produces a variation in the amplitude or other characteristics of the output signal produced by the elastic wave sensor 24. The presence of a defect or flaw may produce a diminished output signal due to attenuated elastic wave transmission between contact points 26 and 28 or may produce an increased output signal due to elastic wave reflections.

Figure 3A:
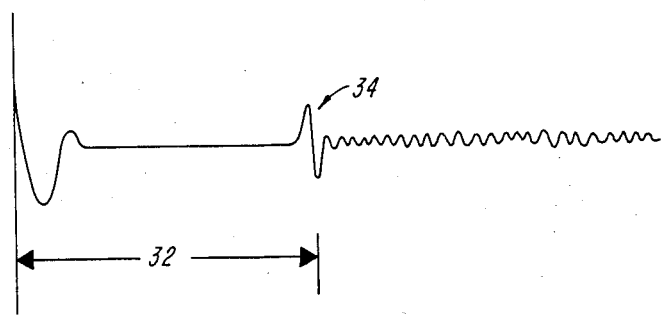
FIGS. 3A and 3B illustrate typical sensor output signals for non-flawed and flawed workpieces, respectively.
Figure 3B:
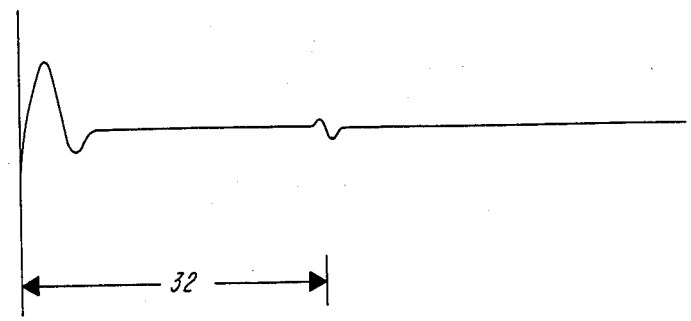

The attenuation effect of a flaw in the workpiece surface 14 on the output signal is illustrated in oscilloscope output traces of FIGS. 3A and 3B. In FIG. 3A, waveguide ends 12 and 20 are in contact with a workpiece surface 14 which is unflawed between points of contact of the respective ends with the workpiece surface 14. After a delay time 32 corresponding to the time of transmission for the elastic wave through the first magnetostrictive waveguide 10 the workpiece surface 14 and the second magnetostrictive waveguide 18 an output pulse 34 occurs representative of elastic waves received at the sensor 24.

As illustrated in FIG. 3B, the presence of a crack or flaw between respective contact points 26 and 28 of the respective first and second magnetostrictive waveguides 10 and 18 results in diminution of the output pulse 34 at delay time 32.

The coils 22 and 24 are slideably mounted over the respective waveguides 10 and 18 to permit the distance between the location of the operator and the actual point of inspection to be varied considerably. It is noted that lengthening the waveguides 10 and 18 results in an increased delay time 32 corresponding to the increased transit time for elastic waves through the respective waveguides and the workpiece surface 14.

Figure 2A:
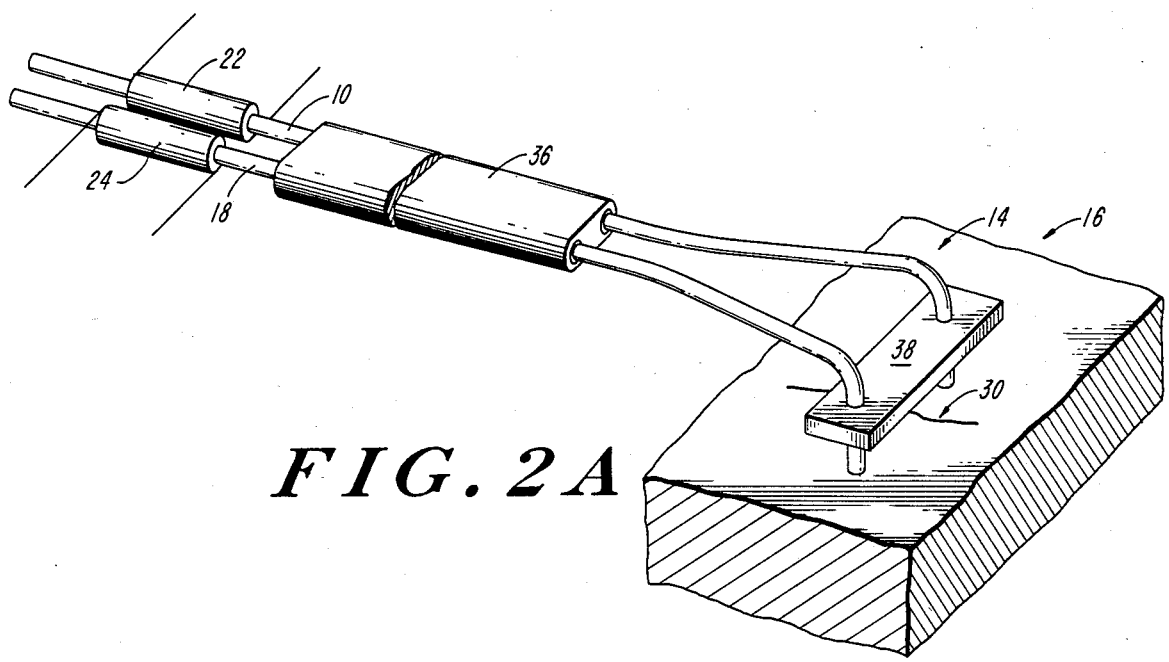
FIGS. 2A and 2B illustrates use of the present invention for detection of defects having differing orientations.
Figure 2B:
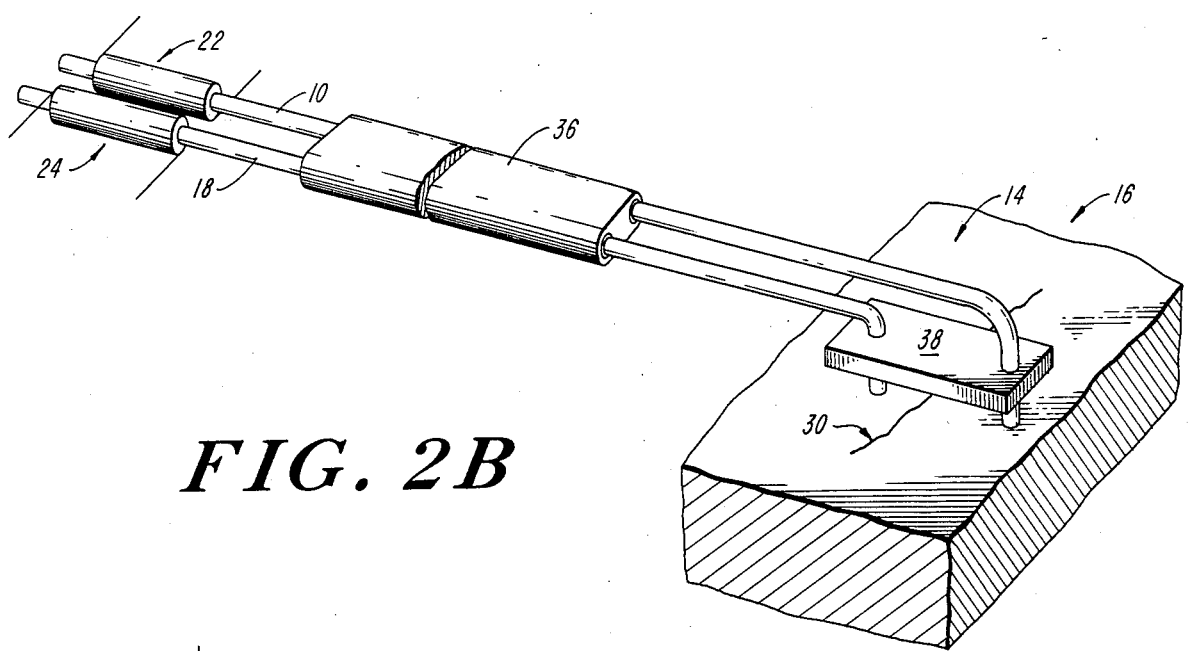

In a preferred embodiment shown in FIG. 2A, the magnetostrictive waveguides 10 and 18 pass through a supporting sheath 36 which provides mechanical support for the relatively thin magnetostrictive waveguides 10 and 18. The sheath 36 is fabricated of a material of substantially different acoustic impedance from the waveguides 10 and 18 to avoid dampening of elastic waves in the respective waveguides due to transmission of elastic waves through the waveguide extending through the sheath 36. Ends 12 and 20 of respective waveguides 10 and 18 are spaced by a pivotable support 38. The orientation of the respective contact points of ends 12 and 20 of the waveguides 10 and 18 is variable. The ends may be vertically disposed as illustrated in FIG. 2A for detection of cracks having a generally horizontal orientation, or by appropriate slideable orientation of the waveguides 10 and 18, ends 12 and 20 of the respective waveguides 10 and 18 may be generally horizontally oriented for detection of workpiece 16 flaw having a substantially vertical orientation as illustrated in FIG. 2B. It is further apparent, that the wavelengths 10 and 18 may be slideably positioned along the workpiece surface and that the support 38 may be pivotably rotated for inspection of the entire surface of a workpiece 16 accessible by a probe in accordance with the present invention. The delay time 32 is indicative of the distance from the elastic wave source and sensor to the defect or waveguide ends.

The respective waveguide ends 12 and 20 may be maintained in physical contact with the workpiece surface by use of any suitable mechanical, electromechanical or magnetic means.

If desired, only a portion of respective waveguides proximate to respective coils may be fabricated of magnetostrictive portions and the magnetostrictive portions may be coupled to nonmagnetostrictive waveguide portions.

Nonmagnetostrictive waveguides may be plated with a magnetostrictive coating to induce and detect elastic waves as previously discussed.

Additionally, excitation and detection of elastic waves in nonmagnetostrictive waveguides may be accomplished employing electrodynamic, piezoelectric or capacitive transducers and elastic waves may be detected with an optical sensor. Elastic waves may also be generated via thermoelastic means.

The above-described invention is illustrative of a novel method and apparatus permitting non-destructive inspection of a workpiece by the use of elastic waves. Other modifications, embodiments, and departures from the present disclosure are possible without departing from the inventive concepts contained herein. Consequently, the invention is to be viewed as embracing each and every novel feature and novel combination of features present in or possessed by the technique and apparatus herein disclosed and are limited solely by the scope and spirit of the appended claims.

What is claimed is:

1. A probe for nondestructive inspection of a workpiece from an operator station, said workpiece having an accessible surface, said probe comprising:
   a first elongated elastic wave waveguide having an end in elastic wave transmitting contact with said workpiece;
   means operative to excite elastic waves in said first elongated waveguide at a location of said first waveguide remote from said end in elastic wave transmitting contact with said workpiece for transmission through said waveguide to said workpiece;
   a second elongated elastic wave waveguide having an end in elastic wave transmitting contact with said workpiece;
   a sheath;
   said first and second waveguides being slidably disposed within said sheath and extending therethrough, said sheath being fabricated of a material to provide an acoustic mismatch between the respective waveguides and the sheath, said sheath providing mechanical support for said waveguide;
   elastic wave detection means disposed on said second waveguide at a location of said second waveguide remote from said end in elastic wave transmitting contact with said workpiece and operative to produce an output signal representative of elastic waves in said second waveguide, said signal corresponding to elastic waves transmitted through said workpiece from said first waveguide end to said second waveguide end;
   the presence and location of a flaw with respect to said waveguide ends in elastic wave transmitting contact with said workpiece and with respect to said workpiece surface being detectable upon analysis of said output signal.

2. The probe of claim 1 wherein said first waveguide comprises a waveguide of magnetostrictive material.

3. The probe of claim 2 wherein said elastic wave exciting means comprises a first coil disposed about said first waveguide, and said exciting means is operative to induce elastic waves in said waveguide via magnetostrictive interaction with said first waveguide upon pulse activation of said first coil.

4. The probe of claim 3 wherein only a portion of said first waveguide first coil comprises a magnetostrictive material.

5. The probe of claim 3 wherein said first coil is slideably disposed about said first magnetostrictive waveguide.

6. The probe of claim 1 wherein said second waveguide comprises a waveguide of magnetostrictive material.

7. The probe of claim 6 wherein said detection means comprises a second coil disposed about said second waveguide, said second coil operative to provide an output signal representative of elastic waves present in said second waveguide.

8. The probe of claim 6 wherein only a portion of said second waveguide comprises a magnetostrictive material.

9. The probe of claim 7 wherein said second coil is slideably disposed about said second magnetostrictive waveguide.

10. The probe of claim 1 wherein said first and second waveguides comprise waveguides of magnetostrictive material.

11. The probe of claim 8 wherein said elastic wave exciting means comprises:
    a first coil disposed about said first waveguide said exciting means being operative to induce elastic waves in said first waveguide via magnetostrictive interaction of said first coil with said first waveguide upon pulse activation of said first coil; and
    said detection means comprises a second coil disposed about said second waveguide, said second coil operative to provide an output signal representative of elastic waves present in said second waveguide.

12. The probe of claim 11 wherein said first and second coils are slideably disposed on said first and second waveguides respectively.

13. The probe of claim 10 wherein each of said first and second magnetostrictive waveguides comprises a nickel wire.

14. The probe of claim 1 including support means for maintaining said workpiece contacting ends of respective first and second waveguide in fixed spatial relation while providing for pivotal rotation of said support means in response to differential longitudinal movement of the respective waveguides.

15. The probe of claim 1 including means for maintaining contact between workpiece contacting ends of said waveguides and said workpiece.

16. The probe of claim 1 wherein each of said waveguides is coated with a layer of magnetostrictive material and said elastic wave exciting means is operative to induce elastic waves in said waveguide via magnetostrictive interaction with said first waveguide upon pulse activation of said elastic wave exciting means.

17. The probe of claim 1 wherein said elastic wave exciting means and elastic wave detection means comprise piezoelectric transducers coupled to said first and second waveguides.

18. The probe of claim 1 wherein said elastic wave exciting means and elastic wave detection means comprise electrodynamic transducers coupled to said first and second waveguides.

19. The probe of claim 1 wherein said elastic wave exciting means is operative to thermoelastically induce elastic waves in said first waveguide.

20. The probe of claim 1 wherein said elastic wave exciting means and detection means comprise capacitive transducers.

21. A probe for nondestructive inspection of a workpiece having an accessible surface, said probe comprising:

a first elongated elastic wave waveguide having an end adapted to be disposed in elastic wave transmitting contact with said workpiece;

means operative to excite elastic waves in said first elongated waveguide at a location of said first waveguide remote from said end adapted to be disposed in elastic wave transmitting contact with said workpiece for transmission of elastic waves through said waveguide to said workpiece;

a second elongated elastic wave waveguide having an end adapted to be disposed in elastic wave transmitting contact with said workpiece;

means for supporting said first and second waveguides in substantially parallel spatial relation, said supporting means being adapted to permit sliding of said first and second waveguides with respect thereto, said supporting means being fabricated of a material to provide an acoustic mismatch with the respective waveguides;

elastic wave detection means disposed on said second waveguide at a location of said second waveguide remote from said end adapted to be disposed in elastic wave transmitting contact with said workpiece and operative to produce an output signal representative of elastic waves in said waveguide, said signal corresponding to elastic waves transmitted through said workpiece from said first waveguide end to said second waveguide end when disposed in elastic wave transmitting contact with said workpiece and upon excitation of elastic waves in said first elongated waveguide;

the presence and location of a flaw in said workpiece with respect to said waveguide ends being detectable upon analysis of said output signal.

* * * * *